United States Patent
Errico et al.

[19]

[11] Patent Number: 5,947,969
[45] Date of Patent: Sep. 7, 1999

[54] ROTATABLE LOCKING VERTEBRAL BODY SCREW, STAPLE AND ROD ASSEMBLY

[75] Inventors: Joseph P. Errico, Far Hills; Thomas J. Errico, Summit; James D. Ralph, Oakland, all of N.J.

[73] Assignee: Third Millennium Engineering, LLC, Summit, N.J.

[21] Appl. No.: 09/174,958

[22] Filed: Oct. 19, 1998

[51] Int. Cl.[6] .................................................. A61B 17/56
[52] U.S. Cl. ................................ 606/61; 606/73; 606/75
[58] Field of Search ................................ 606/61, 60, 72, 606/73, 75; 623/17

[56] References Cited

U.S. PATENT DOCUMENTS 5,620,443  4/1997  Gertzbein et al. ........................ 606/61
5,690,629  11/1997  Asher et al. .............................. 606/61
5,728,127  3/1998  Asher et al. .............................. 606/61

*Primary Examiner*—Guy V. Tucker
*Attorney, Agent, or Firm*—Joseph P. Errico, Esq.

[57] ABSTRACT

A rod, screw, and staple assembly for use in conjunction with anterior or lateral spinal rod implant apparatus includes a vertebral body screw which has a shaft which is insertable into a vertebral bone, a tapered neck, and a head portion which includes a rod receiving channel and an annular recess. The vertebral body staple includes a flat portion which has a hole through it. The hole has a slotted rim which is downwardly sloped so that it may permit the expansion of the hole when a force is applied to it. The screw is advanced into the hole in the staple until the tapered neck thereof snaps through the hole and the rim seats in the annular recess of the screw. This permits the screw and staple to rotate relative to one another, but not to translate axially relative to one another. The staple also includes several barbs which independently hold the staple to the bone surface to which it is to be affixed. The staple may be inserted into the vertebral bone first, and then the screw is driven into the bone through the hole until the neck snaps through the hole. Alternatively, the screw and staple may first be coupled together, and then jointly driven into the bone. In either case, the rod is then inserted into the rod receiving channel and locked in the channel with a nut or set screw.

7 Claims, 2 Drawing Sheets

ROTATABLE LOCKING VERTEBRAL BODY SCREW, STAPLE AND ROD ASSEMBLY

BACKGROUND OF THE INVENTION

1. Field of the Invention

This invention relates generally to a spinal rod fixation apparatus having an elongate rod, a vertebral body screw, and a stabilizing staple element, and more particularly to a rod, screw and staple assembly which is selectively lockable in combination to provide enhanced stability and bone holding strength.

2. Description of the Prior Art

The spinal column is highly complex system of bones and connective tissues which houses and protects critical elements of the nervous system and the arterial and venous bodies in close proximity thereto. In spite of these complexities, the spine is a highly flexible structure, capable of a high degree of curvature and twist through a wide range of motion.

Genetic or developmental irregularities, trauma, chronic stress, tumors, and disease, however, can result in spinal pathologies which either limit this range of motion, or which threaten the critical elements of the nervous system housed within the spinal column. A variety of mechanical implant structures have been disclosed in the art which are used during surgical intervention to immobilize segments of the spine which are either unstable or have, in combination, become so irregular that they threaten the continued health of the patient. These assemblies are generally classified as anterior, posterior, or lateral. As the classifications suggest, posterior implants are attached to the back of the spinal column, generally hooking under the lamina and entering into the central canal, attaching to the transverse process, or coupling through the pedicle bone using pedicle screws. Posterior fixation assemblies using such screws are generally used in short sequence immobilization indications, and generally in the larger, lower lumbar bones, for their attending pathologies. Lateral and anterior assemblies, by contrast are coupled to the anterior portion of the spine, which is the sequence of vertebral bodies, and are often used throughout long segments of lumbar and thoracic sequences of vertebrae. A specific pathology which often requires significant surgical intervention along extended numbers of vertebrae is scoliosis. The present invention relates to spinal fixation devices for immobilizing and altering the alignment of the spine over a large number, for example more than three or four, vertebra by means of affixing at least one elongate rod to the sequence of selected vertebral bodies.

Anterior (and/or lateral) "rod assemblies" of the prior art have generally been inserted into the bone either unicortically or bicortically, wherein the shaft of the screw transects (and gains fixation strength as it passes through) one or two exterior layers of the vertebral bone, respectively. Exposing the tip of the screw shaft through the opposing side of the bone's exterior surface does, however, entail a risk inasmuch as important blood vessels, nerve roots, as well as other critical tissues are often in jeopardy of injury through contact with an exposed screw tip. Bicortical fixation, however, provides greatly enhanced strength against pullout; an event in which the screw is pulled free of the bone as its grip inside the vertebra fails to hold.

In order to provide enhanced stability against such pullout events, a staple as shown in FIG. 1, was designed. The basic staple of the prior art comprises a flat metal surface 10 having a hole 12 formed in the center thereof. The corners 14 of the staple 10 are curved downwardly to form four spaced apart spikes. The basic vertebral body screw 20, rod 30 and top locking nut 40 of the prior art are shown in FIG. 2, in conjunction with the staple 10, in an exploded assembly diagram. The screw 20 is inserted through the hole 12 in the staple 10 until the wider top, rod receiving portion 22 of the screw, contacts and seats in the hole 12 of the staple. The wider base, provided by the staple 10, impairs toggling action by the screw within the bone, and is intended to prevent motion which can cause the screw to bone interface from breaking down. The rod 30 is then placed in the rod receiving channel 24 of the screw head 22, and a top locking nut 40 is advanced onto the top of the screw head 22, thereby locking the rod to the screw 20, and by association, to the bone.

In some advanced embodiments of this screw and staple design (not shown), the hole and the bottom of the screw are designed such that the screw may be inserted at a modest angle to the staple, thus permitting stable seating of the screw and staple, despite slight offsets of the screw relative to the bone surface.

These screw and staple assemblies of the prior are, however, do not prevent the most frequent pullout failure mechanism, which is direct vertical force pullout which is caused when the rod itself imparts a sufficient stress against the shaft to cause the screw to back out of the hole. In addition, the ability of the staple to impair toggling of the screw in the bone is limited insofar as the screw and staple are not held together by any specific means, and therefore does not prevent the screw from rotating in the hole and causing microfractures, which can lead to bone failure. Further, the prior art designs limit the ability of the rod receiving head of the screw to be properly aligned with the rod. In many instances, the screw is not fully seated in the hole of the staple because the screw had to be backed out of the hole by the surgeon to align the rod in the rod receiving channel of the head.

It is, therefore, the principal object of the present invention to provide a vertebral body screw, rod, and staple assembly which provides enhanced stability and pullout protection.

In addition, it is an object of the present invention to provide such an assembly which includes a stable locking of the staple to the screw so that the screw head can be positioned in the ideal orientation without risking the union of the screw and staple.

Accordingly it is also an object of the present invention to provide an assembly in which the staple and screw are coupled together upon completion of the implantation It is also a principal object of the present invention to provide a reliable, durable, and efficient, long term fixation assembly for spine stabilization.

Other objects of the present invention not explicitly stated will be set forth and will be more clearly understood in conjunction with the descriptions of the preferred embodiments disclosed hereafter.

SUMMARY OF THE INVENTION

The preceding objects are achieved by the present invention which is a vertebral body staple, screw and rod assembly, having enhanced stability and pullout strength, in which the staple, the rod and the screw head may be coupled together to form a reliable fixation to the vertebral bone. More particularly, the assembly of the present invention comprises a vertebral body screw having a head which is formed with a rod receiving channel, a rod, a locking means for locking a rod in the rod receiving channel of the head, and a vertebral body staple which couples to the vertebral bone and to the the screw in such a way that the insertion of the screw and staple into the bone permits rotational independence, but does not permit translational independence, thus securing the two members to the bone in concert.

The vertebral body screw of the present invention comprises a shaft and a head. The shaft portion of the screw is designed to be inserted into the vertebral bone, and to firmly anchor the screw to the bone. This fixation is generally enhanced by the shaft including a threading which engages the bone material along its length and prevents axial translation of the shaft along the length of the hole in the bone into which it has been advanced. The head of the screw includes a rod receiving channel which may alternatively be formed vertically in the top of the head or laterally in the side of the head. More particularly, both types of rod receiving channel admit the rod into the head such that the rod extends perpendicularly to the axis of the screw, but in the first instance (the vertical channel), the channel is formed between two upright extending members, and in the second (the lateral channel), the channel is formed in the side of the head. In each embodiment, the upper portion of the head (either the upper portion of the upright extending members or the portion of the head directly above the lateral channel) includes a threading for receiving thereon a top locking nut, or other means for securing a rod within the channel. In the embodiments described in this application, the threading is provided on the inside of the upwardly extending members for receiving a locking set screw.

The exterior of the lower portion of the head curves inwardly to an annular recess. The recess is disposed between the head and the neck of the screw. The neck is comprised of a linearly tapered cuff which narrows from the head to the shaft. This cuff, therefore, has a frustoconical conformation which is coaxial with the shaft of the screw. The function of the curvate lower portion of the head, the annular recess, and the tapered neck shall be explained in greater detail with respect to the assembly of the screw and the staple, however, they are generally provided to rotationally freely couple the screw to the staple (which is described hereinbelow).

The vertebral body staple comprises a member having a flat portion and a plurality of downwardly directed protuberances, generally shaped like spikes or barbs, which extend perpendicularly to the plane formed by the flat portion. The flat portion further includes a hole formed in the center thereof. The hole has a cylindrical rim which is extended downwardly, such that the hole has a tapered cylindrical appearance. This downwardly extending annular rim also has a series of radial slots formed therein such that the application of a dowanward force onto the rim causes the rim segments to deflect, and for the diameter of the hole to increase. This slotted rim is designed to permit the screw shaft to be inserted through the hole and for the tapered neck of the screw to be forcibly advanced through the hole until the rim snaps into the annular recess between the neck and head of the screw. In a preferred embodiment, the upper surface of the rim of the hole in the staple is also curvate, providing a nesting engagement surface on which the lower curved portion of the head seats.

The two alternative methods of surgical implantation and assembly of the present invention are provided as follows. In a first method of implantation, the screw is first advanced into the hole in the staple and coupled such that the screw and staple may freely rotate relative to one another (with the rim seated in the annular recess of the the vertebral body screw). The bone surfaces are then exposed and prepared to receive the screws (one at each bone). The screws are then advanced into the bones at the appropriate angles and to the desired height. As the screws are inserted, and reach a depth such that the tips of the barbs of the staples engage the surface of the bone, the rotational independence of the staple to the screw becomes critical. The staple is advanced into the bone linearly while the screw continues to turn. Once the staple and screw have reached their ideal depth, the rod is placed into the channels of the screw heads, extending along the length of the spinal sequence which is to be immobilized. The locking means, for example a set screw, is then advanced onto the engaging means of the screw head to secure the rod in the channel.

In a second method of implantation and assembly, the staple is inserted into the bone first. The screw is then driven through the hole and into the bone. The tapered neck of the screw provides additional compressive force against the rim of the hole in the staple once the screw reaches a sufficient depth, and ultimately the neck snaps through the hole via deflection of the annular segments around the hole in the staple. The rotational independence of the screw and the staple permit continued linear translation of the staple while the screw is driven the final distance into the bone. Once the screw is in position, the rod is placed in the channel of the head and locked therein.

It shall be understood that the rounded surfaces of the downwardly tapered rim of the hole in the staple and the curved lower portion of the screw head permit the head and the staple to be slightly angularly offset relative to one another without compromising the ideal coupling of the two elements, nor the ideal alignment of either the staple or the screw with the bone.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 1:
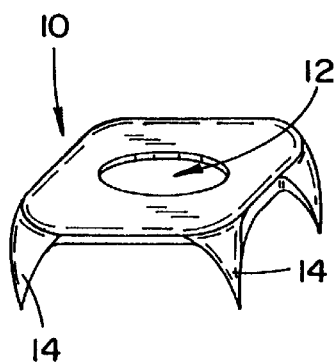
FIG. 1 is a side perspective view of a vertebral body staple of the prior art.
Figure 2:
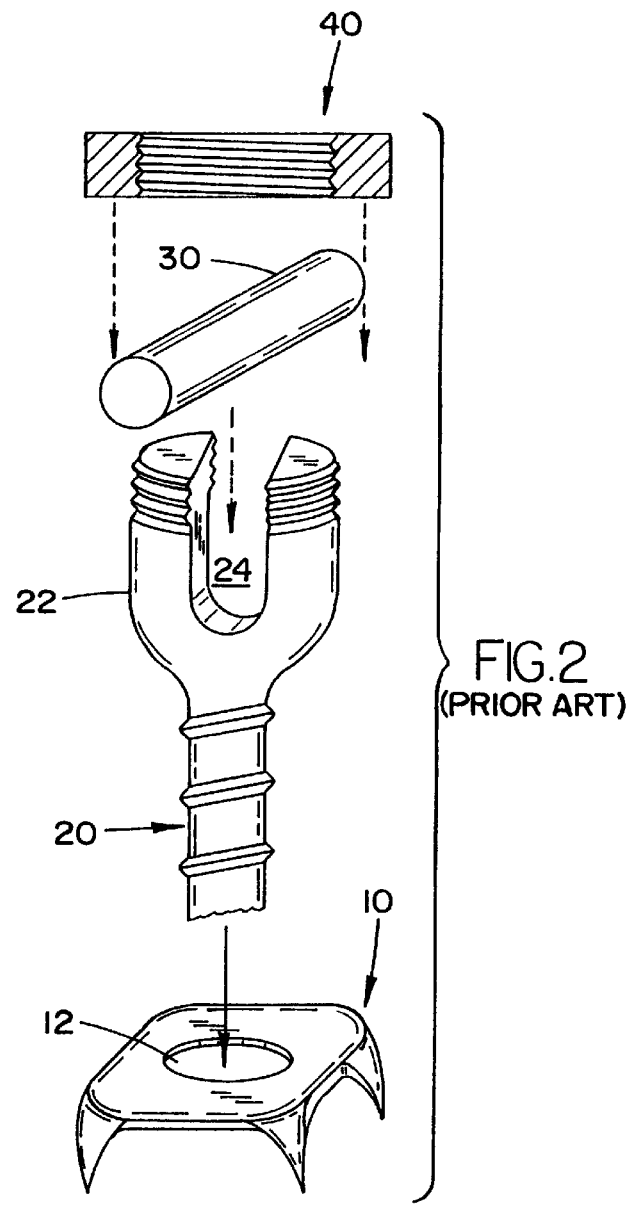
FIG. 2 is an exploded assembly view of a staple, vertebral body screw, rod and top locking nut of the prior art.
Figures 3, 4:
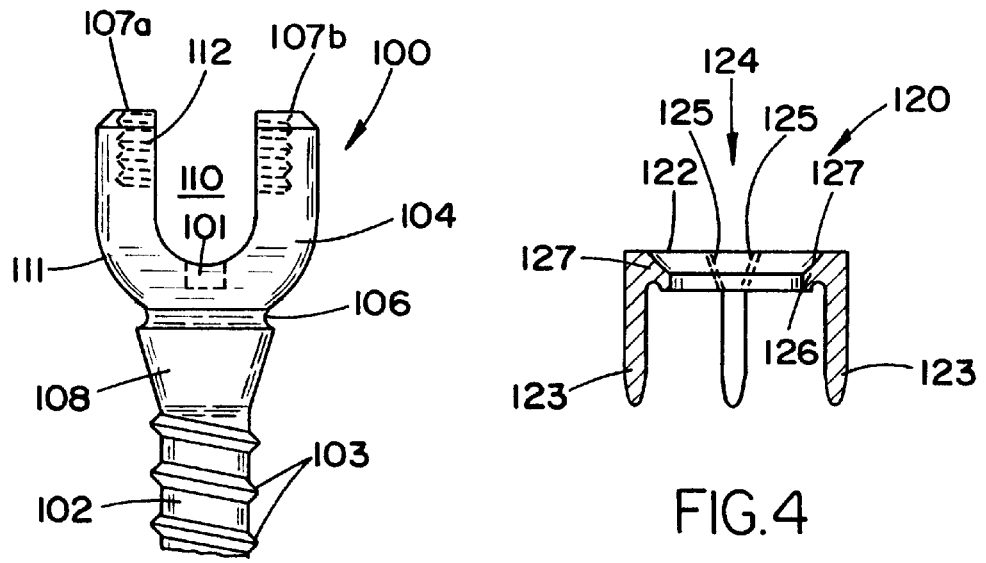
FIG. 3 is a side view of a vertebral body screw which is an aspect of the present invention.
FIG. 4 is a side cross-sectional view of a vertebral body staple which is an aspect of the present invention.

Referring now to FIG. 3, a side view of a vertebral body screw 100 of the present invention, comprising a shaft and a rod coupling head, is shown. The screw 100 comprises a shaft 102, which is threaded, a head portion 104, an annular recess 106, and a tapered neck portion 108. The threading 103 of the shaft is preferably of the type which is suited for high engagement with bone materials, as are well known in the art. It shall be understood that a variety of shaft designs are interchangeable with the present design. The specific choice of shaft features, such as thread pitch, shaft diameter to thread diameter ratio, and overall shaft shape, should be made be the physician with respect to the conditions of the individual patient's bone, however, this invention is compatible with a wide variety of shaft designs.

The head portion 104 comprises a pair of upwardly extending members 107a,107b which define therebetween a rod receiving channel 110. The uppermost interior surfaces of the upwardly extending members 107a,107b include a threading 112 which is ideally suited for receiving a locking set screw (as set forth more particularly with respect to FIG. 5). In alternative designs (not shown), which were introduced above, it is possible to design the rod receiving channel 110 into the side of the upper portion 106 of the head 104, however, the preferred embodiment includes the rod receiving channel 110 in a vertical alignment. In addition, it shall be understood that the use of a set screw is only one possible means for securing a rod in the channel 110, for example, a threading may be disposed on the exterior surfaces of the upwardly extending members 107a,107b and a top locking nut may be employed.

The lower portion of the head 104 comprises a convexly curvate tapered surface 111. This surface 111 is rounded such that it has an overall continuous spherical conformation.

In preferred embodiments, the head further includes a recess 101 in the base of the rod receiving channel 110 which receives a screwdriver such that screw may be advanced into the vertebral bone.

The neck 108 of the screw is linearly tapered such that the diameter of the screw expands from the threaded shaft up to a position beneath the curvately tapered lower surface 111 of the head 104. Between the neck 108 and the head 104 is a recessed annular portion 106 which has a diameter which is less than both the neck and the lower portion of the head 104.

Referring now also to FIG. 4, the vertebral body staple 120 of the present invention is provided in a side cross section view. The staple 120 includes an upper flat surface 122 and a plurality of downwardly directed barbs 123, disposed at the lateral edges of the flat portion 122. The barbs 123, which are intended to be inserted into the vertebral bone surface to provide fixation of the staple to the bone, extend perpendicularly downward from the plane formed by the flat portion 122. The flat portion 122 further includes a hole 124 formed in the center thereof. The hole 124 has a cylindrical rim 126 which extends downwardly and inwardly from the flat surface. This downwardly extending annular rim 126 has a plurality of radial slots 125 formed therein, such that the rim 126 is comprised of a series of segments. The application of a downward force onto the segments causes the overall deflection of the rim such that the hole increases in diameter.

The downward and inward slope of the rim 126 preferably also comprises a concave curvate tapering which, in its undeflected disposition provides a bearing surface 127 having approximately the same curvature as the lower surface 111 of the head 104 of the screw.

The hole 124 in the staple 120 is designed to receive therethrough the shaft of the screw without any interference. The tapered neck 108 of the screw, however, is designed to seat against, and to deflect outwardly, the segments of the rim 126 such that the rim may snap over the neck 108 and seat in the annular recess 106 of the screw.

Figure 5:
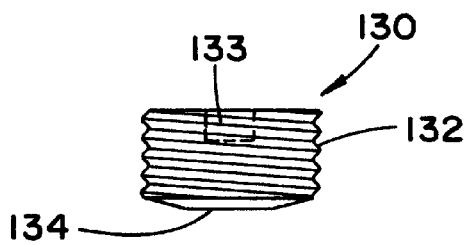
FIG. 5 is a side cross-section view of a top locking set screw which is an aspect of the present invention.

Referring now to FIG. 5, a top locking set screw 130 of the present invention is provided in a side cross section view. The set screw 130 comprises a standard threaded design, having an exterior threading 132 which is matable and advanceable along the interior threading 112 of the head 104 of the vertebral body screw 100. There is also a recess 133 formed in the top of the set screw 130 which is ideally suited for engagement and advancement along the threading 112 of the head 104 of the screw 100 by means of a standard torque applying instrument. The lower surface 134 of the nut 130 is at least partially flat, thus providing a significant surface area over which the downward locking force applied by the nut may be borne.

Figure 6:
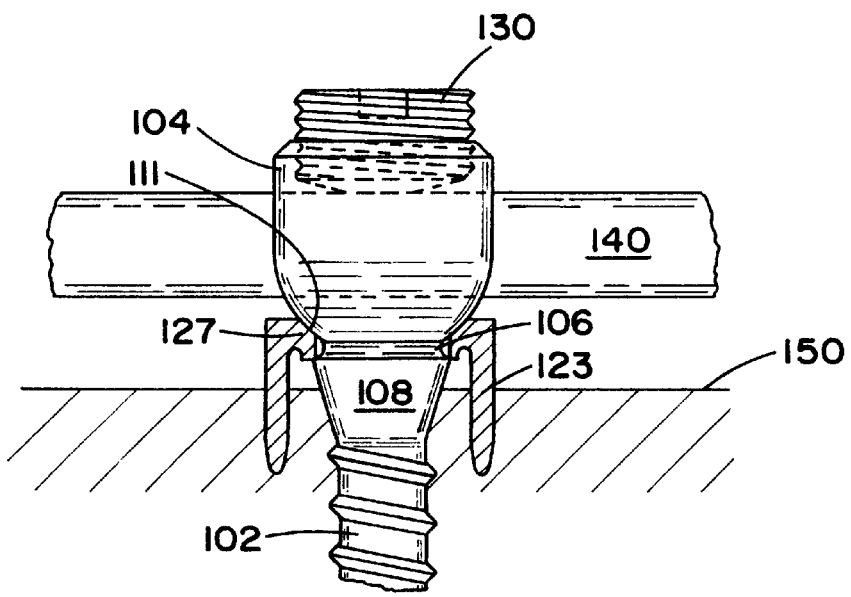
FIG. 6 is a side cross section view of a fully assembled embodiment of the present invention.

Referring now to FIG. 6, a completely assembled embodiment of the present invention is provided in a side cross section view, this view being taken along a direction in which the screw 100 is rotated about its elongate axis by 90 degrees from the orientation illustrated in FIG. 3. The implantation of this device, as well as its functionality and advantages shall be explained in conjunction with the description of the elements and workings set forth in this Figure. There are, however, two alternative methods of implantation and assembly of the present invention, each of which shall be described hereinbelow.

According to the first implantation technique, the staple is positioned against the bone surface 150, and then the barbs 123 are driven into the bone. The screw 100 is then driven through the hole 124 in the staple 120 until the neck 108 snaps through the deflecting hole and the rim 126 seats in the annular recess 106 of the screw. In this configuration, the screw and staple are coupled such that each may rotate relative to the other, but relative axial translation is inhibited. As the screw is further advanced into the bone, the lower surface 111 of the head 104 of the screw seats against the bearing surface 127 of the staple. The curvatures of the bearing surface 127 and the lower surface 111 of the screw head 104 permits modest angular offsets of the staple and screw without preventing full seating of the screw head in the staple 120. Subsequent insertion and locking of the rod 140 in the rod receiving channel 110 of the screw 100 rigidly couples the assembly to the bone, and immobilizes the intended vertebral sequence.

In the second method of implantation and assembly, the screw 100 and the staple 120 are coupled together prior to the insertion of either into the bone. More particularly, the screw is inserted through the hole in the staple until the rim of the staple spins freely about the annular recess of the screw. The screw is then driven into the bone until the barbs 123 of the staple 120 contact the bone surface. Continued rotational advancement of the screw into the bone causes the linear translation of the staple into the bone (and a relative rotation of the screw with respect to the staple). As above, the curvature of the interface between the lower surface 111 of the screw and the curvate rim segements 127 of the staple 120 permit modest offsets of the staple and the screw. Subsequent insertion and locking of the rod 140 in the rod receiving channel 110 of the screw 100 rigidly couples the assembly to the bone, and immobilizes the intended vertebral sequence While there has been described and illustrated embodiments of a rod, vertebral body screw and staple assembly for use with anterior or lateral spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A vertebral body screw and staple assembly for use with orthopedic rod implantation apparatus, comprising:

a vertebral body staple having first and second portions thereof, said first portion including means for direct fixation of the staple to vertebral bone, said second portion having a throughhole formed therein, said second portion further including a plurality of radial slots extending outwardly from said throughhole;

a vertebral body screw having a shaft which is insertable into a vertebral bone, a head portion which includes a rod receiving channel and an annular recess, and a tapered neck portion which is forcibly insertable through the throughhole in said staple by deflection of the radial slots; and means for securing a rod in said rod receiving channel;

wherein the staple and the screw are rotationally independent, but axially coupled such that when jointly inserted into the bone the staple may be inserted linearly as the screw is rotationally advanced into the bone.

2. The vertebral body screw and staple assembly as set forth in claim 1, wherein said means for direct fixation of the staple to vertebral bone comprises a plurality of downwardly extending barbs.

3. The vertebral body screw and staple assembly as set forth in claim 1, wherein said head of said vertebral body screw further includes a curvate lower portion and the staple includes a corresponding curvate taper of the radial slotted portion such that the lower portion of the screw seats in the radial slotted portion of the staple.

4. The vertebral body screw and staple assembly as set forth in claim 1, wherein said means for securing a rod in said rod receiving channel comprises a set screw which mates to a threading formed on the head portion of the screw.

5. A vertebral body screw and staple assembly for use with orthopedic rod implantation apparatus, comprising:

a vertebral body staple having a portion thereof which is flat, said flat portion having an upper surface and a lower surface, said staple further having a plurality of vertebral bone fixation protuberances extending downwardly therefrom, said flat portion further including a throughhole formed therein which includes a rim having a plurality of radial slots formed therein such that the throughhole may expand or contract in accordance with the application of a force applied thereto;

first means for securing a rod in a rod receiving channel;

a vertebral body screw having a shaft portion, a tapered neck, an annular recess, and a rod receiving head portion, said rod receiving head portion including a rod receiving channel formed therein, said shaft being insertable through said throughhole in said staple, said tapered neck being forcibly insertable through said throughhole by causing a deflection of said radial slots, said head portion of said screw being larger than the maximum deflected diameter of said throughhole, and said annular recess being narrower than said throughhole such that once advanced into said recess said staple may rotate independent of said screw, but not translate axially relative to said screw.

6. The vertebral body screw and staple assembly as set forth in claim 1, wherein said head portion of said vertebral body screw further includes a curvate lower portion and the staple includes a corresponding curvate taper of the radial slotted portion such that the lower portion of the screw seats in the radial slotted portion of the staple.

7. A vertebral body screw and staple assembly for use with orthopedic rod implantation apparatus, comprising:

a vertebral body staple having a throughhole formed in a flat surface thereof, said throughhole having a radially slotted rim;

a vertebral body screw having shaft, tapered neck, and head portions, said head portion including a rod receiving channel and an annular recess;

means for securing a rod in said rod receiving channel;

said staple being mountable in the annular recess of said head portion of said screw such that the staple and the screw may rotate relative to one another, but may not translate axially relative to one another, such that the insertion of the screw and staple into a vertebral bone, and a rod is inserted into said rod receiving channel, and the application of said means for securing the rod in the rod receiving channel causes the screw, the staple, and the rod to be locked together in a fully secured combination.

* * * * *